United States Patent [19]
Reich

[11] Patent Number: 6,037,783
[45] Date of Patent: *Mar. 14, 2000

[54] PROCESS FOR DETERMINING THE SOLIDS CONTENT OF A GAS FLOW

[76] Inventor: Ernst Reich, Glasbachweg 15, D-79410 Badenweiler, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/894,043

[22] PCT Filed: Feb. 9, 1996

[86] PCT No.: PCT/EP96/00564

§ 371 Date: Aug. 11, 1997

§ 102(e) Date: Aug. 11, 1997

[87] PCT Pub. No.: WO96/24838

PCT Pub. Date: Aug. 15, 1996

[30] Foreign Application Priority Data

Feb. 11, 1995 [DE] Germany ............................ 195 04 544

[51] Int. Cl.[7] .................................................. G01N 31/53
[52] U.S. Cl. ........................ 324/639; 324/71.4; 73/34.02; 73/24.03
[58] Field of Search ..................................... 324/71.4, 639, 324/641, 642; 73/28.01, 24.02, 24.03, 24.06, 861.04, 861.08

[56] References Cited

U.S. PATENT DOCUMENTS

| | | | |
|---|---|---|---|
| 4,512,200 | 4/1985 | Ghering et al. | 73/861.04 |
| 4,566,321 | 1/1986 | Zacchio | 324/78.5 |
| 4,718,269 | 1/1988 | Der Kinderen | 73/28.01 |
| 4,726,235 | 2/1988 | Leffert et al. | 73/861.04 |
| 5,341,101 | 8/1994 | Maerefat et al. | 324/376 |
| 5,502,393 | 3/1996 | Yamaguchi et al. | 324/639 |
| 5,550,537 | 8/1996 | Perdue | 324/642 X |
| 5,581,191 | 12/1996 | Yamaguchi | 324/639 X |

*Primary Examiner*—Michael Brock
*Attorney, Agent, or Firm*—Bachman & LaPointe, P.C.

[57] ABSTRACT

In a process for determining the solids content of a gas flow, in particular for regulating the firing of a boiler with coal dust in a coal-fired power plant, electromagnetic waves are sent from a transmitter (20) to a receiver (21) through the solids-laden gas flow. The attenuation of these electromagnetic waves due to the absorption of part of them by the solids is then determined.

13 Claims, 4 Drawing Sheets

PROCESS FOR DETERMINING THE SOLIDS CONTENT OF A GAS FLOW

The invention relates to a method for determining the charging of a gas stream with solid fractions, in particular for regulating the firing of a boiler with coal dust in a coal-fired power station, and to a device for this purpose.

In many sectors of industry, it is necessary to transport solid fractions by means of a gas stream. In the present case, the primary concern is to measure and regulate the supply of coal dust to the boiler of a coal-fired power station. However, this is to be merely a preferred exemplary embodiment of the present invention.

In coal-fired power stations known at the present time, coal dust is fed by carrier air to corresponding burners which are arranged at different levels in a boiler. Furthermore, combustion air also enters the boiler and assists the combustion of the coal dust in the boiler.

For the purpose of setting the quantity of coal-dust particles which is supplied, flaps, distributors or such actuating members are employed in a corresponding, feed conduit, these being set once, namely on the commissioning of the coal-fired power station, and then remaining in this position for a relatively long period of time.

Sampling from the feed stream is then carried out at specific periods for the purpose of resetting the firing. An incorrect setting of the firing is not recognized because, at the present time, the quantity of coal-dust particles can be measured only discontinuously. However, the supply of an incorrect quantity of coal-dust particles to the boiler has a highly adverse effect. On the one hand, the efficiency is appreciable lowered and, on the other hand, the waste gas values are increased. Furthermore, as a consequence of an incorrect quantity of coal-dust particles, the boiler and also the burner are subject to increased wear.

The use of measuring instruments in the feedstream itself would also be conceivable, but the disadvantage of this is that the feedstream is contracted in the region of the measuring instrument, so that pressure losses or abrasion occur here. Both are undesirable.

The object on which the present invention is based is to develop a method and a device of the above-mentioned type, by means of which a continuous determination of the solid fractions in a gas stream becomes possible in a simple manner, without this gas stream being in any way impaired.

To achieve this object, electromagnetic waves are sent from a transmitter to a receiver through the gas stream having the solid fractions, and the attenuation of these electromagnetic waves as a result of the absorption of some of them on the solid fractions is determined.

The great advantage of this method is, on the one hand, that it is possible continuously to subject the gas stream having the solid fractions to the electromagnetic waves. Continuous measurement of the solid fractions may accordingly take place. Furthermore, there is no need, for example in a sensor tube, for mechanical fittings which lead to the above-mentioned disturbance of the gas stream.

The invention makes use of the advantage of electromagnetic waves that parts of these electromagnetic waves are reflected and absorbed on solid fractions. That is to say, these parts do not arrive at the receiver, so that a considerable difference is detected between the electromagnetic waves transmitted and those received. The charging of the gas stream with solid fractions can be deduced from this difference, this, of course, initially being only of relative value. Evaluating the relative measurement by means of a correcting factor gives an absolute measurement.

This could be carried out, for example, as follows:

The throughput capacity and/or the quantity are recorded on an apron conveyor, by means of which coal is fed to a mill for the production of coal dust. This can take place by means of commercially available measuring systems, for example by means of a radiometric conveyor weigher.

The sum of the individual measurements of the coal-dust stream in the burner conduits or the sensor tubes is formed, in order thereby to determine the total throughput capacity and/or quantity.

The correcting factor for obtaining an absolute measurement from the relative measurement of the coal-dust stream is calculated from:

$$C = \frac{\text{throughput capacity (quantity apron conveyor)}}{\text{throughput capacity (quantity individual measurement)}}$$

Each measured value is evaluated from the individual measurements by means of this correcting factor.

However, as a rule, the relative values are sufficient for regulating the firing of a boiler with coal dust in a coal-fired power station, the relative values of the individual feed conduits to the individual burners being compared with one another.

A further or additional possibility for measuring the charging of a gas stream with solid particles is to determine a change in amplitude of the electromagnetic waves transmitted. This method makes use of the action of the reflection effect, The amplitude of a reflected frequency-shifted electromagnetic wave signal, especially a microwave signal, is also a measure of the charging of the gas stream and may be utilized as such for signal evaluation.

Both transmitters and receivers for electromagnetic waves are commercially available. Mention is made here, purely as an example, that the transmitter may be a Gunn oscillator. By contrast, for example, a Schottky diode in a cavity resonator may be used for the receiver. These are, however, merely exemplary embodiments.

In a preferred exemplary embodiment, the electromagnetic waves are reflected several times on their path between the transmitter and receiver. Por example, in a sensor tube for coal-dust particles, this takes place through the metal walls of this tube. Accordingly, there is provision for the transmitter and also the receiver of the electromagnetic waves to be inclined in or opposite to the direction of flow. In the case of a specific angle of inclination and a specific distance between the transmitter and the receiver, it is possible, for example, for three-fold reflection to take place in the sensor tube, thereby appreciably increasing the attenuating effect, so that the difference between the transmitted waves and received waves can be increased and consequently represented more clearly. Three-fold reflection is therefore to be viewed merely as an example, and, of course, once-only reflection, straight passage or multiple reflection may also be sufficient in individual cases.

Microwaves with a frequency of above 1 GHz are preferably used as electromagnetic waves.

If the charging of a gas stream is determined by means of the amplitude of the reflected frequency-shifted microwave signal, it is appropriate to integrate the transmitter and receiver in one antenna. This antenna then transmits the corresponding electromagnetic waves preferably perpendicularly to the gas stream, so that these waves are reflected on the opposite inner wall of the feed pipe and are received again by the same antenna. The same also applies to those waves which are reflected by the solid fractions.

In a preferred exemplary embodiment, not only the charging of the gas stream with solid fractions is determined, but also their velocity. Interlinking the two signals produces the throughput signal. This is carried out by designing the transmitter at the same time as the receiver. This receiver receives the waves reflected back directly from the individual coal-dust particles, a frequency shift being produced as a result of the Doppler effect. The two frequencies, that is to say the transmitted frequency and the reflected frequency, differ only slightly from one another. The velocity can be determined from the frequency difference.

It is known, furthermore, that, due to the funnel-shaped design of the antenna, the electromagnetic waves also penetrate conically into the sensor tube. However, this means that dead spaces, in which no waves are absorbed or reflected, occur on the left and right of this cone. Precisely in these dead spaces, however, the gas stream could possibly be charged with a different solid fraction.

So as also to determine the solid fraction in these dead spaces, an insert is to be inserted in the orifice of the sensor tube, through which orifice the electromagnetic wave cone penetrates into the sensor tube, said insert giving rise to a lens effect. That is to say, this insert also disperses the electromagnetic waves toward the side, so that the dead spaces are eliminated.

The insert is preferably composed of two layers. One layer is composed of a material, through which electromagnetic waves experience no attenuation, this layer being curved on the tube side, thus bringing about the lens effect. This layer is preferably composed of a low-loss plastic.

Toward the tube, this layer is also covered with a low-attenuation layer, for which purpose fusion basalt, which protects the plastic lens from abrasion, is preferably used.

As an alternative to the two-part lens, a one-part lens made of ceramic may also be used.

If the reflection method is employed for charging measurements, the place of installation of the antenna plays a decisive role in the functioning of the measuring operation. In this case, the place of installation must be selected so that the distribution of the solids in the tube is as homogeneous as possible. This is afforded, for example, in the region of a tube bend or downstream of a diffuser introduced into the tube.

It also depends on the homogeneity of the solid flow whether measurement can be carried out with or without the lens insert described above.

The entire method can also be carried out in already existing coal-fired power stations. The device is easy to integrate. The measuring system merely has to be coupled to a regulator which receives the corresponding desired values from outside. According to the comparison between the actual and desired values, the regulator can then activate corresponding adjusting members, such as flaps or valves.

Further advantages, features and details of the invention emerge from the following description of preferred exemplary embodiments and with reference to the drawing in which.

Figure 1:
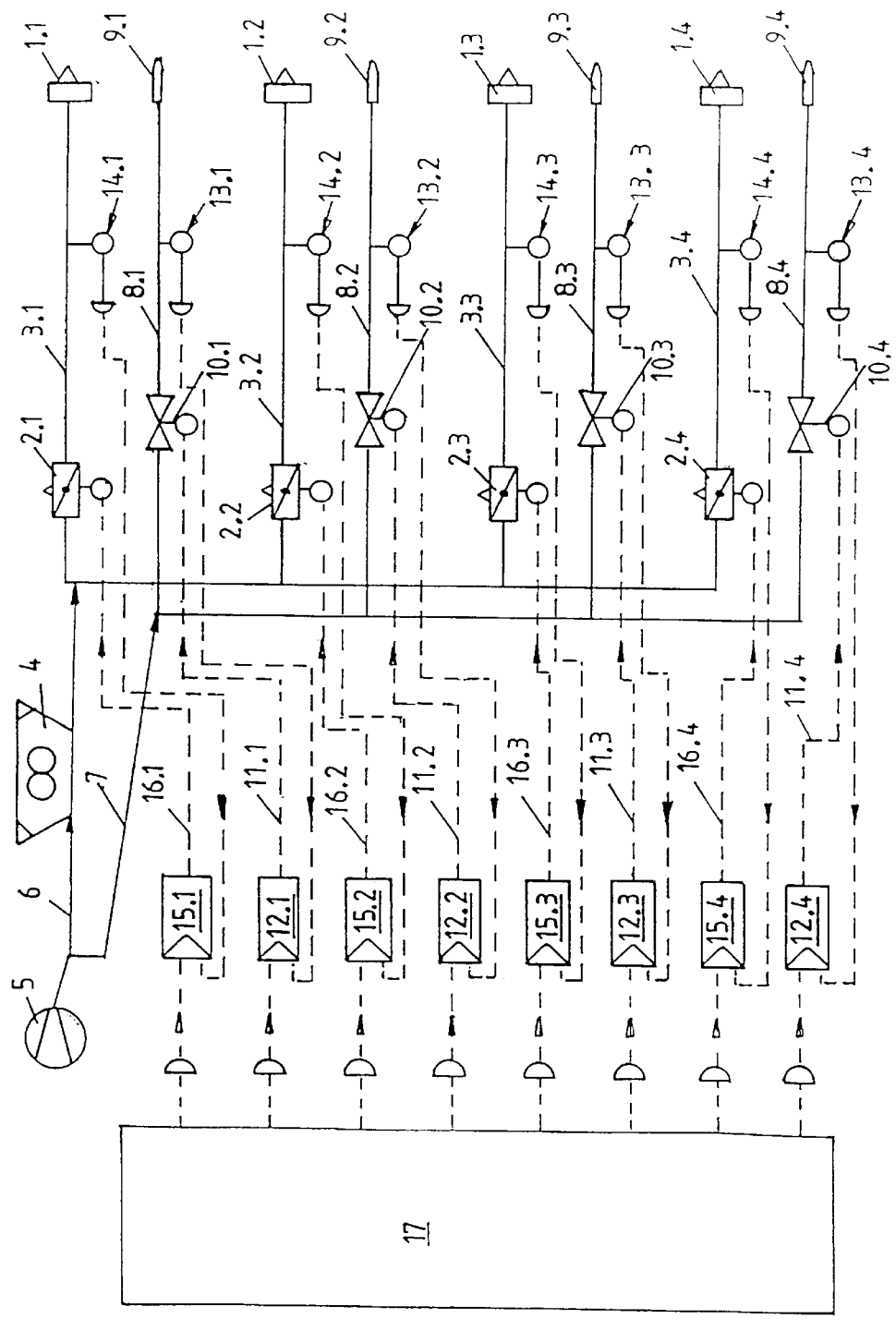
FIG. 1 shows a block diagram of a method according to the invention for regulating the firing of a boiler with coal dust in a coal-fired power station.

According to FIG. 1, in a boiler of a coal-fired power station, said boiler not being shown in any more detail, a plurality of burners, here 1.1 to 1.4, are arranged in each case at different levels. Each burner 1 is connected to a coal mill 4 via a feed conduit 3.1 to 3.4, an actuating member 2.1 to 2.4 being inserted at a suitable point in each case into the conduit between the coal mill 4 and the burners 1.1 to 1.4.

The coal dust is transported, from a discharge of the coal mill 4, said discharge not being shown in any more detail, through the actuating member 2 and the feed conduit 3 to the burner 1 with the aid of carrier air. In this case, the carrier air is generated by a blower 5.

A combustion air conduit 7 branches off from a carrier air conduit 6 between the blower 5 and coal mill 4 and divides into individual branch conduits 8.1 to 8.4, each branch conduit 8.1 to 8.4 being connected to a nozzle 9.1 to 9.4. Each nozzle 9.1 to 9.4 is assigned in each case to a burner 1.1 to 1.4 and supplies the burner region with combustion air.

Inserted into each branch conduit 8.1 to 8.4 is an actuating member 10.1 to 10.4 which is connected to a regulator 12.1 to 12.4 via a control line 11.1 to 11.4. This regulator receives values from a measuring point 13.1 to 13.4 which determines a throughflow of combustion air between the actuating member 10.1 to 10.4 in the nozzle 9.1 to 9.4.

A measuring point 14.1 to 14.4 is also provided in a similar way between the actuating member 2.1 to 2.4 of the burner 1.1 to 1.4, said measuring point in each case transmitting values to a further regulator 15.1 to 15.4. Each regulator 15.1 to 15.4 is connected to the actuating member 2.1 to 2.4 via a further control line 16.1 to 16.4.

The corresponding desired values for regulating the actuating members 2.1 to 2.4 and 10.1 to 10.4 are preset for the regulator 12.1 to 12.4 and 15.1 to 15.4 by a control 17.

Figure 2:
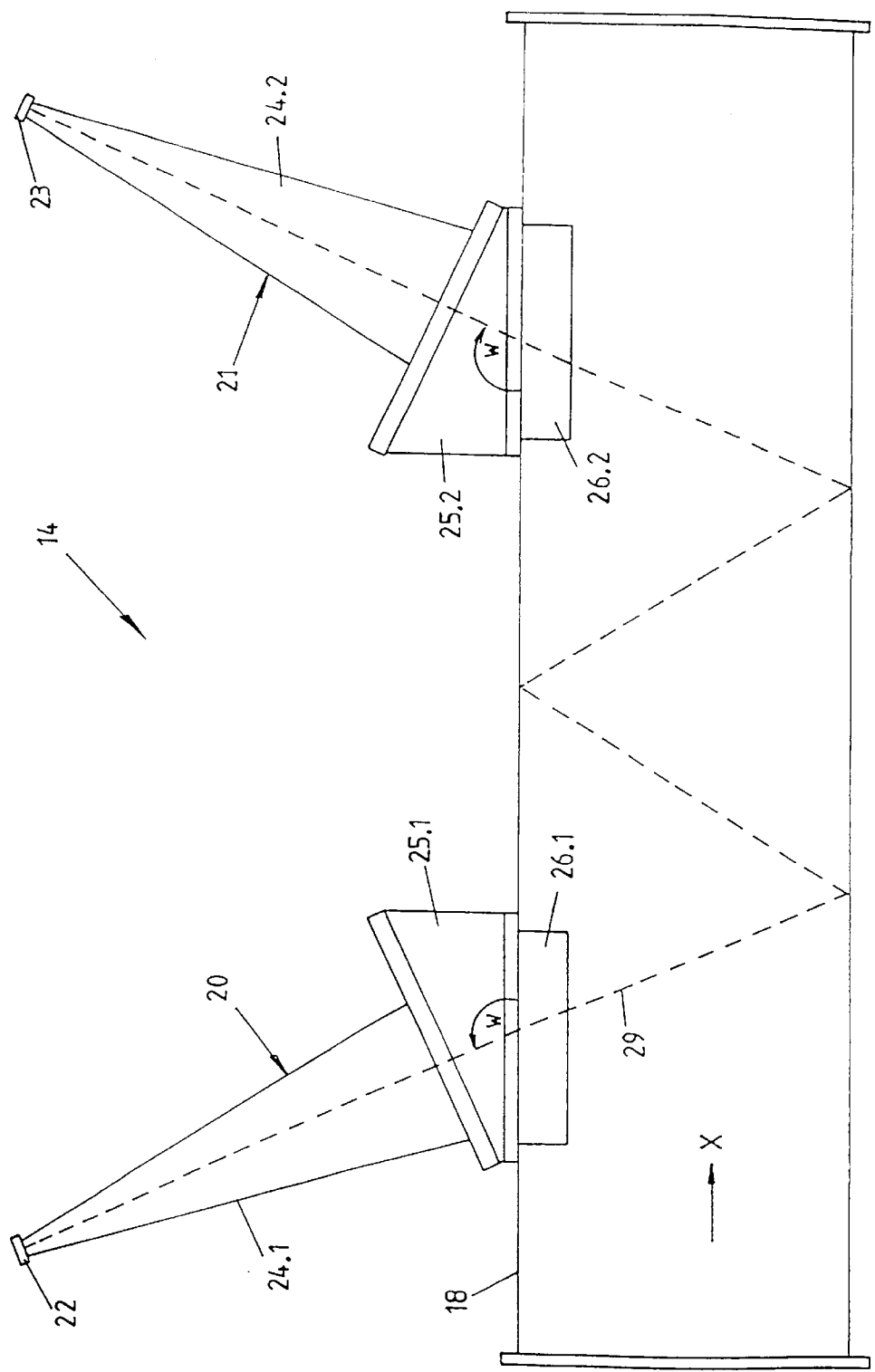
FIG. 2 shows an enlarged detail from FIG. 1 in the region of a measuring point.

While the pure combustion air throughput can be determined in any known way at the measuring points 13.1 to 13.4, the measurement of the coal dust at the measuring points 14.1 to 14.4 is determined in a novel inventive way. One of these measuring points 14 is shown, enlarged, in FIG. 2.

A transmitter 20 for a microwave, on the one hand, and a receiver 21 for this microwave, on the other hand, are attached to a sensor tube. The transmitter 20 is preferably a Gunn oscillator in a cavity resonator, while, in the case of the receiver 21, a Schottky diode is arranged in a cavity resonator.

In a preferred exemplary embodiment, moreover, the transmitter 20 is designed at the same time as the transmitter and receiver, as also described later.

The Gunn element 22 or the Schottky diode 23 has adjoining it a funnel-shaped antenna 24.1 or 24.2 which is attached to an angle housing 25.1 or 25.2. This angle housing 25.1 or 25.2 is connected to the sensor tube 18 via connecting shells 26.1 or 26.2. The sensor tube 18 is cut out in this region, so that an orifice 27 (see FIG. 3) is obtained between the interior 28 and the antenna 24.1 or 24.2.

By virtue of the design of the angle housing 25.1 or 25.2, the transmitter 20 is set at an angle w of above 90° to the sensor tube 18. The angle w ensures that the electromagnetic wave 29, indicated by broken lines, enters the sensor tube 18 in the feed direction of the coal dust, is reflected threefold on the walls in this sensor tube 18 and then enters the receiver 21 which is set at the angle w opposite to the feed direction x. There, the electromagnetic wave is recorded by the Schottky diode and a voltage corresponding to this electromagnetic wave is generated in the Schottky diode.

This measuring point 14 functions as follows:

The fundamental idea is based on the attenuation of a beam of an electromagnetic wave by the coal dust. The electromagnetic wave should have a frequency range f greater than 1 GHz. When the waves impinge on the coal particles, this microwave range brings about a spin effect in the ferromagnetic elements, thus resulting in beam attenuation. This process is referred to as ferromagnetic resonance absorption. A transmitter 20 and receiver 21 for the electromagnetic waves are directed into the sensor tube 18. In this case, a measurement of the beam attenuation produced by the coal dust is made.

Setting the transmitter 20 and receiver 21 at an angle w achieves a multiplication of the beam distance. In the case of three-fold reflection, as in the present instance, an increase in the attenuating effect is thereby achieved over a specific distance. This results in a substantially higher measuring sensitivity.

However, an essential feature of the present invention is also that the flight velocity of the coal particles is recorded at the same time. This is carried out by utilizing the Doppler effect, in which case, as already mentioned above, the transmitter is also designed at the same time as the receiver. For example, a Schottky diode could also at the same time be arranged in the transmitter 20 in addition to the Gunn element. Other embodiments are also conceivable here, however, transmitters/receivers of this type being obtainable commercially.

Due to the inclined arrangement of the transmitter 20, microwaves impinge on individual coal-dust particles. They are reflected there, so that some of the transmitted waves can be received again by the receiver part of the transmitter 20. This reflection of the wave transmitted at a constant frequency of, for example, 24,125 GHz produces a frequency shift as a consequence of the Doppler effect. Since the two frequencies differ from one another only slightly (by approximately 1 to 2 kHz), a difference signal, which can be uncoupled at the transmitter, is obtained. This uncoupled frequency can be determined as follows:

$$\Delta f = 2 \frac{v \cdot \cos\alpha}{c} f_o,$$

in which v=material velocity

α=setting angle $f_o$=transmitted frequency

Δf=frequency shift c=light velocity

Figure 3:
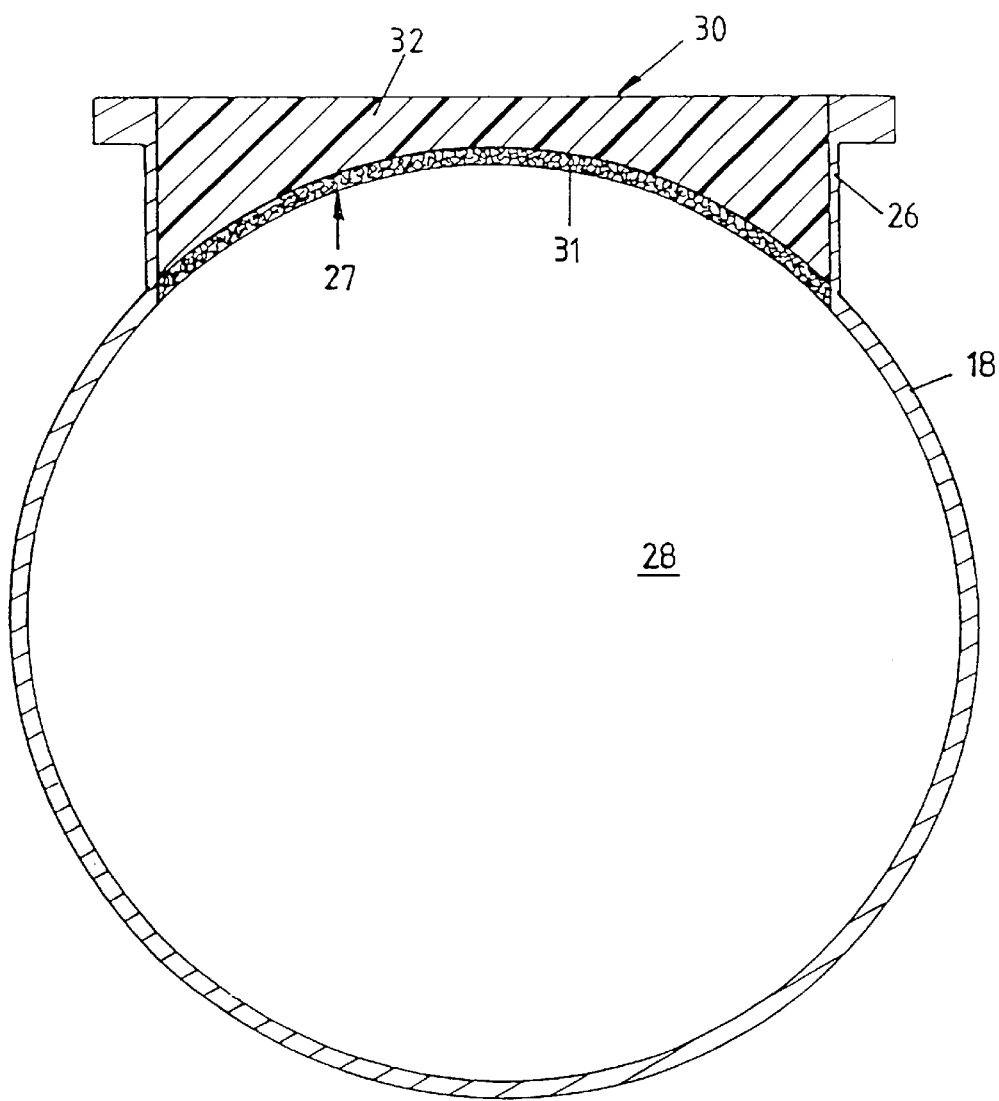
FIG. 3 shows a cross section through a sensor tube in the region of the measuring point according to FIG. 2.

In a further preferred exemplary embodiment according to FIG. 3, an insert 30 is inserted into the orifice 27 formed in the sensor tube 18 by the connecting shell 26, said insert giving rise to a lens effect. The purpose of this lens effect is to disperse the transmitted electromagnetic waves within the sensor tube 18 in such a way that dead spaces occur as little as possible.

The insert 30 preferably has a double-layered design. An inner arched shell 31 is composed of a material having low attenuation of the electromagnetic waves. Fusion basalt is preferably used here. Arranged above this is a plastic layer 32 which does not attenuate the electromagnetic waves at all.

Figure 4:
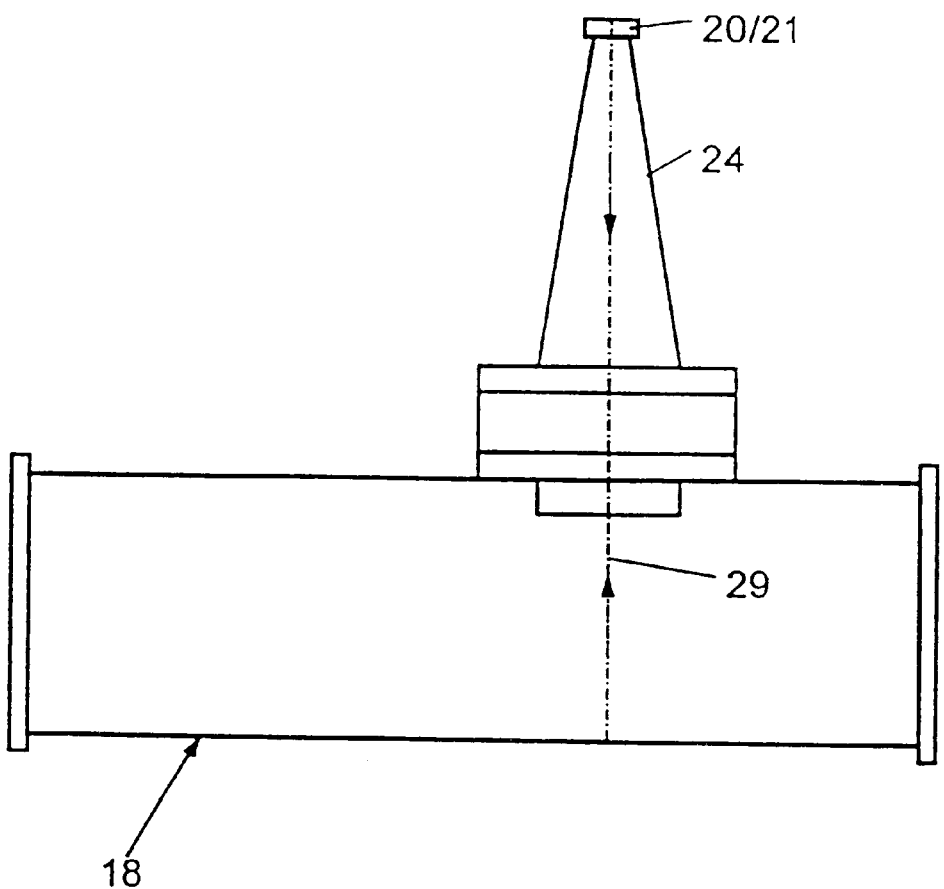
FIG. 4 shows a diagrammatically illustrated detail in section through another exemplary embodiment of a measuring point.

The above-mentioned Doppler effect, by means of which the flight velocity of the coal particles is determined, is also utilized by the exemplary embodiment of the method according to the invention, as shown in FIG. 4. There, the transmitter and receiver 20/21 are integrated in one antenna 24, this antenna 24 or the electrical wave 29 running, for example, perpendicularly to the feed tube 18. That is to say, this wave 29 impinges on the opposite inner wall of the feed tube 18 and is reflected back again perpendicularly. If this wave impinges on a coal particle moved in the feed tube 18, said wave is reflected, and, on the one hand, the above-mentioned frequency shift takes place, but, on the other hand, the reflected wave also has a different amplitude. The amplitude of the reflected frequency-shifted microwave signal is a measure of the charging of the gas stream and can thus be utilized as such for signal evaluation. The charging of a gas stream can consequently be determined not only via the attenuation of the microwave signal passing through, but also via the amplitude of the directly reflected microwave.

I claim:

1. A device for determining the charging of a gas stream with solid fractions for regulating the firing of a boiler with coal duct in a coal-fired power station, comprises:

a sensor tube (18) through which a gas stream having solid fractions flows;

a transmitter (20) for generating electromagnetic waves is connected to the sensor tube (18) by an antenna (24.1), an angle housing (25.1) and connecting shell (26.1), the connecting shell (26.1) enclosing an orifice (27) in the sensor tube (18) said orifice having an insert (30) arranged in the orifice for producing a lens affect; and a receiver (21) seated on the sensor tube to receive said electromagnetic waves.

2. Device according to claim 1, characterized in that the insert (30) is composed of a shell (31) composed of a layer (31) having low attenuation of the electromagnetic waves and of a layer (32) transmitting electromagnetic waves in an unimpeded manner.

3. Device according to claim 2, characterized in that the low-attenuation layer (31) is composed of fusion basalt and the nonattenuating layer (32) is composed of plastic.

4. Device according to claim 1, characterized in that the insert (30) is produced in one piece from ceramic.

5. Device according to claim 1, characterized in that the receiver (21) for electromagnetic waves is integrated in the transmitter (20) to form a unit.

6. Device according to claim 5, characterized in that the transmitter/receiver unit (20,21) is arranged in such a way that a transmitted and reflected electromagnetic wave (29) runs perpendicularly to the gas stream.

7. Device according to claim 1, characterized in that the transmitter (20) and receiver (21) are arranged on a feed tube (18) at a point where the distribution of the solids in the tube is as homogeneous as possible.

8. Device according to claim 7, characterized in that the transmitter (20) and receiver (21) are used in the region of a tube bend.

9. Device according to claim 7, characterized in that the transmitter (20) and receiver (21) are used downstream of a diffuser introduced into the tube.

10. A device for determining the charging of a gas stream with solid fractions for regulating the firing of a boiler with coal duct in a coal-fired power station, comprises:

a sensor tube (18) through which a gas stream having solid fractions flows;

a transmitter (20) for generating electromagnetic waves connected to the sensor tube by an orifice (27) having an insert (30) arranged in the orifice for producing a lens affect, the insert (30) is composed of a shell composed of a layer having low attenuation of the electromagnetic waves and of a layer transmitting electromagnetic waves in an unimpeded manner wherein the low attenuation layer is composed of fusion basalt and the nonattenuation layer is composed of plastic; and a receiver (21) seated on the sensor tube to receive said electromagnetic waves.

11. Device according to claim 10, characterized in that the transmitter (20) is connected to the sensor tube (18) via an antenna (24.1), an angle housing (25.1) and a connecting shell (26.1), the connecting shell (26.1) enclosing said orifice (27) in the sensor tube (18).

12. Device according to claim 11, characterized in that the receiver (21) is also connected to the sensor tube (18) via an antenna (24.2), an angle housing (25.2) and a connecting shell (26.2), the connecting shell (26.2) enclosing an orifice (27) in the sensor tube (18).

13. Device according to claim 12, characterized in that the transmitter (20) and receiver (21) are arranged so as to be inclined at an angle (w) with respect to the axis (x) of the sensor tube.

* * * * *